US008702682B2

(12) United States Patent
Atanasoska et al.

(10) Patent No.: US 8,702,682 B2
(45) Date of Patent: Apr. 22, 2014

(54) MEDICAL DEVICES EMPLOYING PIEZOELECTRIC MATERIALS FOR DELIVERY OF THERAPEUTIC AGENTS

(75) Inventors: Liliana Atanasoska, Edina, MN (US); Rajesh Radhakrishnan, Maple Grove, MN (US); Scott Schewe, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 476 days.

(21) Appl. No.: 13/020,663

(22) Filed: Feb. 3, 2011

(65) Prior Publication Data
US 2011/0196347 A1 Aug. 11, 2011

Related U.S. Application Data

(60) Provisional application No. 61/301,862, filed on Feb. 5, 2010.

(51) Int. Cl.
*A61K 9/22* (2006.01)

(52) U.S. Cl.
USPC .. 604/890.1; 604/19; 604/93.01; 604/103.01; 604/103.02; 604/182; 623/1.42

(58) Field of Classification Search
USPC ............ 604/19–22, 48, 93.01, 96.01, 103.01, 604/103.02, 131, 151, 153, 182, 289, 890.1, 604/891.1; 623/1.1–1.22, 1.42, 1.43; 417/413.2
See application file for complete search history.

(56) References Cited

U.S. PATENT DOCUMENTS

| 4,568,851 | A | 2/1986 | Soni et al. | |
|---|---|---|---|---|
| 5,614,549 | A | 3/1997 | Greenwald et al. | |
| 5,733,925 | A | 3/1998 | Kunz | |
| 6,322,532 | B1 * | 11/2001 | D'Sa et al. | ...................... 604/22 |
| 6,730,699 | B2 | 5/2004 | Li et al. | |
| 2003/0176836 | A1 * | 9/2003 | Doukas et al. | ............. 604/93.01 |
| 2005/0055014 | A1 * | 3/2005 | Coppeta et al. | ............ 604/890.1 |
| 2005/0129727 | A1 | 6/2005 | Weber et al. | |
| 2005/0165439 | A1 | 7/2005 | Weber et al. | |
| 2006/0079836 | A1 | 4/2006 | Holman et al. | |
| 2006/0142706 | A1 * | 6/2006 | Roy et al. | ...................... 604/296 |
| 2006/0184092 | A1 | 8/2006 | Atanasoska et al. | |
| 2007/0239256 | A1 | 10/2007 | Weber et al. | |
| 2008/0125851 | A1 * | 5/2008 | Kilpatrick et al. | ........... 623/1.13 |

FOREIGN PATENT DOCUMENTS

WO 2007070790 6/2007

OTHER PUBLICATIONS

E. Smela et al., "Volume Change in Polypyrrole Studied by Atomic Force Microscopy," J. Phys. Chem. B, 105 (2001) 9395-9405.
J. Causley et al., "Electrochemically-induced fluid movement using polypyrrole," Synthetic Metals 151 (2005) 60-64.
J. Zhao et al., "Synthesis of thin films of barium titanate and barium strontium titanate nanotubes on titanium substrates," Materials Letter 59 (2005) 2329-2332.

(Continued)

*Primary Examiner* — Kami A Bosworth
(74) *Attorney, Agent, or Firm* — Fish & Richardson P.C.

(57) ABSTRACT

In one aspect, the present invention provides therapeutic-agent-releasing medical devices which comprise at least one region of piezoelectric material. Therapeutic agent release is initiated or increased when the piezoelectric material is subjected to mechanical stress, which leads to the development of a voltage across the piezoelectric material. This voltage is used to initiate or increase therapeutic agent release.

15 Claims, 7 Drawing Sheets

(56) References Cited

OTHER PUBLICATIONS

N.W. Emanetoglu et al., "MgxZn1-xO: A New Piezoelectric Material," Proc. IEEE 2001 Int. Ultrasonics Symposium, vol. 1, pp. 253-256, 2001.

N.W. Emanetoglu, IEEE Transactions on Ultrasonics, Ferroelectkics; and Frequency Control; vol. 50; No. 5, May 2003, 537-543.

"Piezoelectric Polymers," 33 pages, date unknown but not later than Oct. 17, 2008.

F.M. Guillot et al., "Piezoelectric Fabrics for Energy Harvesting," National Textile Center Research Briefs: Jun. 2007, NTC Project: F06-GT05, pp. 1-3.

M.T. Cortes et al., "Artificial muscles based on conducting polymers," e-Polymers 2003, No. 041, 1-42.

S.N. Fedosov, "Switching of polarization and relaxation phenomena in corona poled ferroelectric polymers," Physics and Chemistry of Solid State, vol. 3, No. 3 (2002) pp. 413-417.

J. Snyder and B. Lewandowski, "Resonant Frequencies of Implantable Piezoelectric Generators," National Aeronautics and Space Administration, 18 pp., date unknown but no later than Mar. 24, 2009.

B. Lewandowski et al., "Design Considerations for an Implantable, Muscle Powered Piezoelectric System for Generating Electrical Power" Annals of Biomedical Engineering, vol. 35, No. 4, Apr. 2007 pp. 631-641.

T. Starner et al., "Human Generated Power for Mobile Electronics" Low Power Electronics Design, CRC Press, Summer 2004, 28 pp.

Z.L. Wang et al., "Piezoelectric Nanogenerators for Self-Powered Nanodevices," Persuasive Computing, vol. 7, No. 1, Jan.-Mar. 2008, 49-55.

K.S. Shankar et al., "Fabrication of nanowires of multicomponent oxides: Review of recent advances," Materials Science and Engineering C 25 (2005) 738-751.

F.D. Morrison et al., "High-aspect-ratio piezoelectric strontium—bismuth-tantalate Nanotubes," J. Phys.: Condens. Matter 15, L527-L532 (2003).

Z. Wan et al., "Piezoelectric Micropump for Drug Delivery" Jun. 4, 2001, pp. 1-5.

K. Junwu et al., "Design and test of a high-performance piezoelectric micropump for drug delivery," Sensors and Actuators A 121 (2005) 156-161.

A.S. Zurkinden et al., "Wave Energy Converter through Piezoelectric Polymers," Excerpt from the Proceedings of the COMSOL Users Conference 2007 Grenoble, 7 pages.

T.L. Jordan et al., Piezoelectric Ceramics Characterization, NASA Langley Research Center, Hampton, Virginia, Sep. 2001, ICASE Report No. 2001-28, 1-22.

E. Fukada, "New Piezoelectric Polymers," Jpn. J. Appl. Phys., vol. 37 (1998), 2775-2780.

Rashidian, B. and Allen, M.G., "Integrated Piezoelectric Polymers for Microsensing and Microactuation Applications," American Society of Mechanical Engineers Dynamic Systems and Control Division, vol. 32, pp. 171-179, ASME, New York, NY 1991 (from the 1991 ASME Winter Annual Meeting, Atlanta, GA).

L. Wang et al., "Formation of ordered macroporous films from fluorinated polyimide by water droplets templating," European Polymer Journal 43 (2007) 862-869.

Liang W-J. et al., "Morphology and Ionic Conductivity Studies of Hybrid Electrolytes based on Epoxide-Crosslinked Polysilane/Polyether Networks," Macromol. Chem. Phys. 2004, 205, 600-610.

Jaber G. Quasem et al., "Kinetics of Paclitaxel 2'-N-methylpyridinium Mesylate Decomposition," AAPS PharmSciTech 2003, 4(2) Article 21.

E.W. Damen et al., "Paclitaxel esters of malic acid as prodrugs with improved water solubility," Bioorg Med Chem., Feb. 2000, 8(2), pp. 427-432.

R. Duncan et al., "Polymer-drug conjugates, PDEPT and PELT: basic principles for design and transfer from the laboratory to clinic," Journal of Controlled Release 74 (2001) 135-146.

C. Li, "Poly(L-glutamic acid)—anticancer drug conjugates," Advanced Drug Delivery Reviews 54 (2002) 695-713.

R. Duncan, "The Dawning Era of Polymer Therapeutics," Nature Reviews/Drug Discovery, vol. 2, May 2003, 347-360.

I.L. Radtchenko et al., "A novel method for encapsulation of poorly water-soluable drugs: precipitation in polyelectrolyte multilayer shells," International Journal of Pharmaceutics, 242 (2002) 219-223.

Dr. Sabar D. Hutagalung, Piezoelectric Ceramics, date unknown but not later than Mar. 24, 2009.

\* cited by examiner

MEDICAL DEVICES EMPLOYING PIEZOELECTRIC MATERIALS FOR DELIVERY OF THERAPEUTIC AGENTS

RELATED APPLICATIONS

This application claims priority from U.S. provisional application 61/301,862, filed Feb. 5, 2010, which is incorporated by reference herein in its entirety.

FIELD OF THE INVENTION

The present invention relates to medical devices, including medical devices for the delivery of therapeutic agents into subjects.

BACKGROUND

The delivery of a therapeutic agent onto or within the body of a patient is common in the practice of modern medicine. In vivo delivery of therapeutic agents is often implemented using medical devices that may be temporarily or permanently placed at a target site within the body. These medical devices can be maintained, as required, at their target sites for short or prolonged periods of time, delivering therapeutic agents at the target site.

SUMMARY

In one aspect, the present disclosure provides therapeutic-agent-releasing medical devices which comprise at least one region of piezoelectric material. Therapeutic agent release may be initiated or increased when the piezoelectric material is subjected to mechanical stress, which leads to the development of a voltage across the piezoelectric material.

This voltage may be used to initiate or increase therapeutic agent release. For instance, in some embodiments, the voltage may be used to create or enlarge an aperture through which the therapeutic agent can pass. In other embodiments, the voltage may be used to drive the electrical migration of a charged therapeutic agent.

An advantage of the present disclosure is that medical devices may be provided in which therapeutic agent delivery is controllable by the application of mechanical stress.

These and other aspects, embodiments and advantages of the present disclosure will become readily apparent to those of ordinary skill in the art upon review of the Detailed Description and any claims to follow.

DETAILED DESCRIPTION

Figure 1A:
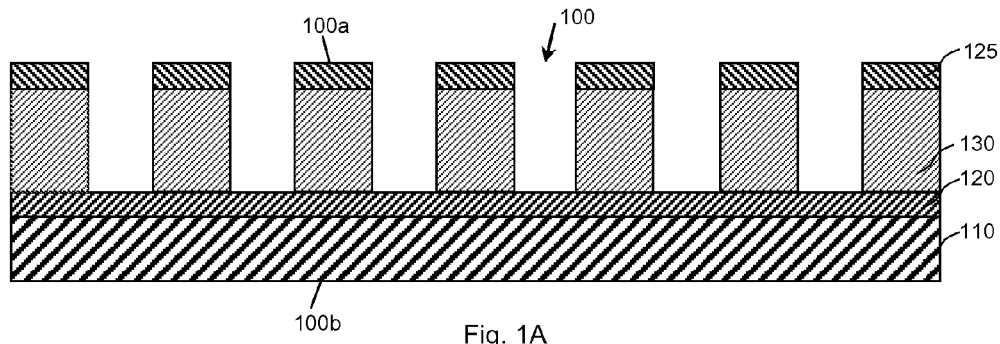
FIG. 1A is a partial schematic cross-sectional view of the device of FIG. 1B, taken along line A-A.

A more complete understanding is available by reference to the following detailed description of various aspects and embodiments of the invention. The detailed description which follows is intended to illustrate but not limit the invention. The scope of the invention is defined by any appended claims.

Material regions (e.g., piezoelectric regions, conductive regions, non-conductive regions, therapeutic-agent-containing regions, etc.) for use in the present invention may be formed in a near infinite variety of shapes and sizes. In various embodiments of the invention, material regions are provided in the form of layers. As used herein a "layer" of a given material is a region of that material whose thickness is small (e.g., 25% or less) compared to both its length and width. As used herein a layer need not be planar, for example, taking on the contours of an underlying substrate. Layers can be discontinuous (e.g., patterned). Terms such as "film," "layer" and "coating" may be used interchangeably herein.

Piezoelectricity is the ability of certain materials to generate an electric potential in response to applied mechanical stress (e.g., compressive stress, tensile stress, shear stress, etc.). This may take the form of a separation of electric charge across the material. If the material is not short-circuited, a voltage is established across the material. Without wishing to be bound by theory, in various materials, the positive and negative electrical charges are separated, but symmetrically distributed, so that the material overall is electrically neutral. Each of these sites forms an electric dipole and dipoles near each other tend to be aligned in regions called Weiss domains. The domains are usually randomly oriented, but can be aligned during poling, a process by which a strong electric field is applied across the material, usually at elevated temperatures. Regardless of the theory of operation, when a mechanical stress is applied to the resulting material, a voltage is established across the material.

Examples of piezoelectric materials include ceramic materials and polymeric materials. Examples of known piezoelectric ceramic materials include those that comprise the following: barium titanate ($BaTiO_3$), lead titanate ($PbTiO_3$), $Bi_{0.5}Na_{0.5}TiO_3$, lead zirconate titanate ($Pb[Zr_xTi_{1-x}]O_3$ $0<x<1$), commonly known as PZT, potassium niobate ($KNbO_3$), lithium niobate ($LiNbO_3$), $K_{0.5}Na_{0.5}NbO_3$, lithium tantalate ($LiTaO_3$), sodium tungstate ($Na_2WO_3$), $Ba_2NaNb_5O_5$, $Pb_2KNb_5O_{15}$, and $Mg_xZn_{x-1}O$, among others. Examples of piezoelectric polymers include poly(vinylidene fluoride) (PVDF), poly(vinylidene fluoride-co-trifluoroethylene), also referred to as P(VDF-TrFE), polyvinylchloride (PVC), polyvinylfluoride (PVF), and odd-numbered polyamides (nylon 5, nylon 7, nylon 9, nylon 11, etc.), among others. Examples of piezoelectric materials further include polymer-ceramic composite materials that combine piezoelectric polymers and piezoelectric ceramics, such as those above. Such materials can combine the piezoelectric strength of ceramics with the ease of processing associated with polymers.

In accordance with one aspect of the invention, medical devices are provided which comprise at least one region of piezoelectric material and from which therapeutic agent release is initiated or increased when the piezoelectric material is subjected to mechanical stress. More particularly, the application of the stress leads to the development of a voltage across the piezoelectric material as discussed above, which voltage is used to initiate or increase therapeutic agent release. For instance, the voltage may be used to create or enlarge an aperture through which the therapeutic agent can diffuse, or the voltage may be used to drive the electrical migration of a charged therapeutic agent, among other possibilities.

Numerous designs are possible for implementing therapeutic agent release via piezoelectric materials. For example, in certain embodiments of the invention, a medical device is provided which comprises a first conductive region, for example, in the form of a conductive substrate. The substrate may be inherently conductive (e.g., a metallic or conductive polymer substrate) or the substrate may be non-conductive (e.g., formed from a non-conductive polymeric or ceramic material) and rendered conductive (e.g., by forming a metallic region on the substrate). In these embodiments, a suitably poled piezoelectric material is disposed on the first conductive region such that a lower surface of the piezoelectric material is in electrical contact with the first conductive region. A second conductive region (e.g., in the form of a metallic layer) is disposed on an upper surface of the piezoelectric material, but does not contact the first conductive region (so as to avoid short circuiting).

When the device is administered to a subject (e.g., contacted with the subject, inserted into the subject, implanted in the subject, etc.) and a mechanical stress is applied to the piezoelectric material (e.g., when the material is subjected to compression between the first and second conductive regions), a voltage is created between the first and second conductive regions. The voltage may be used to initiate or increase a rate of release of the therapeutic agent from the device into the subject In some embodiments, the resulting voltage may be used to create or enlarge an aperture through which the therapeutic agent can diffuse. For example, the therapeutic agent may be held within the medical device by a corrodible barrier layer and the voltage may be used to accelerate corrosion of the barrier layer, thereby forming one or more apertures (e.g., pores, holes, etc.) in the barrier layer or increasing the size of preexisting apertures in the barrier layer (e.g., pores, holes, etc., that are present in the manufactured device), allowing release of the therapeutic agent to be initiated or increased.

Examples of materials that may be used to form corrodible barrier layers include corrodible metals and metal alloys and corrodible non metals. Specific examples include corrodible metals such as, for instance, calcium, magnesium, zinc and iron, and corrodible metal alloys such as, for instance, alloys magnesium, zinc and/or iron (including their alloys with combinations of each other and other metals such as Ce, Ca, Zr, Li, etc., for example, alloys containing magnesium and one or more of Fe, Ce, Ca, Zn, Zr and Li, alloys containing iron and one or more of Mg, Ce, Ca, Zn, Zr and Li, alloys containing zinc and one or more of Fe, Mg, Ce, Ca, Zr and Li, etc.), among others.

As another example, the therapeutic agent may be held within the medical device by a barrier layer that comprises an aperture that is partially or completely swollen shut by uptake of one or more chemical species. The voltage generated by applying mechanical stress to the piezoelectric material may be used to expel the chemical species, increasing the size of the aperture (i.e., opening and/or enlarging the aperture) and allowing the therapeutic agent to be released.

For example, an aperture within a conductive polymer layer may be swollen shut or nearly shut by uptake of ions, and the voltage generated by the piezoelectric material may be used to expel the ions, increasing the size of the aperture.

Known conductive polymers suitable for the invention include polypyrrole and its derivatives and copolymers, polythiophene and its derivatives and copolymers, including poly (3-alkyl thiophenes) and poly(3,4-ethylenedioxythiophene) (PEDOT), polyaniline and its derivatives and copolymers, poly(p-phenylene vinylene) and its derivatives and copolymers, polysulfone and its derivatives and copolymers, and polyacetylene and its derivatives and copolymers.

Polypyrrole is one of the more stable of these polymers under physiological conditions. Derivatives of polypyrrole include the following substituted polymers: poly(N-methylpyrrole), poly(N-butylpyrrole), poly[N-(2-cyanoethyl)pyrrole], poly[N-(2-carboxyethyl)pyrrole], poly(N-phenylpyrrole), poly[N-(6-hydroxyhexyl)pyrrole], and poly[N-(6-tetrahydropyranylhexyl) pyrrole], among others. Examples of pyrrole copolymers include, for example, poly[pyrrole-co-3-(acetic acid)pyrrole], poly[pyrrole-co-1-(propionic acid) pyrrole], poly[pyrrole-co-1-(propionic acid)pyrrole pentafluorophenol ester], poly[pyrrole-co-1-(2-cyanoethyl) pyrrole] and poly(pyrrole-co-1-phenylpyrrole), among others.

Conductive polymers are typically semi-conductors in their neutral state. However, upon oxidation or reduction of the polymer to a charged state (e.g., polypyrrole is positively charged when oxidized and is neutral when reduced), the electrical conductivity is understood to be changed from a semi-conductive regime to a semi-metallic regime. Without wishing to be bound by theory, oxidation and reduction are believed to lead to charge imbalances that, in turn, can result in a flow of ions into or out of the material. These ions typically enter/exit the material from/into an ionically conductive medium adjacent to the polymer (e.g., electrolyte solutions, bodily fluids and tissues, etc.). It is generally believed that dimensional changes are effectuated in conductive polymers by the mass transfer of the ions into or out of the polymers. For example, in some conductive polymers, expansion is believed to be due to ion insertion between chains, whereas in others, inter-chain repulsion is believed to be the dominant effect. Regardless of the mechanism, this ion movement results in expansion or contraction of the polymer which can deliver significant stresses and strains. For example, E. Smela et al., "Volume Change in Polypyrrole Studied by Atomic Force Microscopy," *J. Phys. Chem. B*, 105 (2001) 9395-9405, have reported an increase in film thickness by over 35% for polypyrrole in the reduced state compared to the oxidized state.

Redox switching of conductive polymers may allow a number of different oxidation states to be accessible. These redox states are stabilized by charge-balancing counter ions, which move in and out of the polymer during electrochemical switching. As a specific example, a variety of charge-balancing anions may be associated with an oxidized, positively charged, conductive polymer, such as polypyrrole, for example, during electropolymerization. By reducing/neutralizing the polymer, a net negative charge develops within the polymer. If the dopant anions are substantially mobile (e.g., where the anions are small molecules), the development of the net negative charge upon reduction/neutralization of the polypyrrole results primarily in expulsion of the anions from the polymer into an adjacent ionically conductive medium, shrinking the polymer. Examples of mobile ions that are commonly used in the formation of polypyrrole include perchlorate ($ClO_4^-$), $BF_4^-$, $Br^-$, $Cl^-$, $NO_3^-$, and $I^-$. Naturally occurring ions (in the body) such as chloride ions may be preferred from a biological point of view. If the dopant anions are substantially immobile (e.g., where the anions are large molecules), the development of the net negative charge upon reduction/neutralization of the polypyrrole results primarily in an influx of cations from an adjacent ionically conductive medium, expanding the polymer. Examples of substantially immobile anions that are commonly used in the formation of polypyrrole include dodecylbenzene sulfonate, polyvinyl sulfonate, poly-4-styrene sulfonate, polyaspartic acid, and polyglutamic acid. Examples of mobile cations include naturally occurring (in the body) cations such as $Na^+$ and $K^+$, among others.

It is noted that dodecylbenzene sulfonate is a surfactant having a hydrophilic (charged) end and hydrophobic (hydrocarbon) end. Reduction/neutralization of polypyrrole in which dodecylbenzene sulfonate is used as the dopant ion has been observed to cause an increase in hydrophilicity, which has been hypothesized to be the result of the repulsion of the charged end of the surfactant from the polymer bulk to the surface (i.e., the interface with the ionically conductive medium), such that the concentration of the hydrophilic charged end groups increases at the surface. Conversely, oxidation of the of polypyrrole has been observed to cause an increase in hydrophobicity, which has been hypothesized to be the result of withdrawal of the charged end of the surfactant into the polymer bulk, leading to an increase in concentration of the hydrophobic end of the surfactant at the surface. Regardless of the mechanism, dodecylbenzenesulfonate-doped polypyrrole is observed to swell and become more hydrophilic upon reduction/neutralization and is observed to shrink and become more hydrophobic upon oxidation. See, e.g., J. Causley et al., "Electrochemically-induced fluid movement using polypyrrole," *Synthetic Metals* 151 (2005) 60-64.

Various conductive polymers can be formed by electropolymerization. For instance, pyrrole monomers may be electropolymerized in the presence of a suitable anionic material (e.g., one of the anionic doping materials discussed above, among others).

For further information regarding conductive polymers, see, e.g., Pub. Nos. US 2006/0184092 to Atanasoska et al. and US 2007/0239256 to Weber et al., as well as the references cited therein.

As previously noted, in accordance with various aspects of the invention, medical devices are provided in which the application of the stress leads to the development of a voltage across a piezoelectric material, which voltage is used to initiate or increase therapeutic agent release. Such medical devices may comprise, for example, a first conductive region in contact with a first surface of a suitably poled piezoelectric material and a second conductive region in contact with a second surface (e.g., an opposing surface) of the piezoelectric material. When a mechanical stress is applied to the piezoelectric material (e.g., when the material is subjected to a compression), a voltage is created between the first and second conductive regions, which voltage may be used to initiate or increase therapeutic agent release. In some embodiments, this voltage is used to increase or retard the delivery of a charged therapeutic agent.

Like other ionic species, charged therapeutic agents move in response to concentration gradients (via a process called "diffusion") and in response to electric fields (via a process called "migration"). In the present invention, such an electric field may be created by applying mechanical stress to the piezoelectric material. For example, a therapeutic-agent-containing region that comprises a charged therapeutic agent may be placed in contact with one of the first and second conductive regions, but not the other. The piezoelectric region may be designed (e.g., based on the polling direction) such that, when placed under compression (e.g., compressed between the first and second conductive regions), either the first conductive region will become positively charged while the second conductive region becomes negatively charged or the first conductive region will become negatively charged while the second conductive region becomes positively charged. In these embodiments, the charge of the therapeutic agent in the therapeutic-agent-containing region may be of the same charge as the charge that is developed at the conductor with which the therapeutic-agent-containing region is in contact, leading to electrostatic repulsion of the charged therapeutic agent during compression. Conversely, the charge of the therapeutic agent in the therapeutic-agent-containing region may have a charge that is opposite to the charge that is developed at the conductor with which the therapeutic-agent-containing region is in contact, leading to electrostatic retention of the charged therapeutic agent during compression.

In some embodiments, the therapeutic-agent-containing region consists of substantially pure therapeutic agent (e.g., 90 wt % or more).

In some embodiments, the therapeutic-agent-containing region comprises a charged therapeutic agent within a material that temporarily delays release of the therapeutic agent (e.g., due to the fact that the therapeutic agent is not on the surface). For example, a charged therapeutic agent may be provided within a porous matrix material (e.g., a polymeric, ceramic, metallic, etc. porous matrix material). A macroporous membrane may be applied to the device for this purpose. For example, among many other possibilities, various types of polymers can be fabricated as a honeycomb-patterned film with controlled pore size, ranging from hundreds of nanometers to hundreds of microns as described in L. Wang et al., "Formation of ordered macroporous films from fluorinated polyimide by water droplets templating," *European Polymer Journal* 43 (2007) 862-869. By using a porous matrix material, the bulk of the therapeutic agent is expected to remain within the porous material until the time that the piezoelectric material is compressed for delivery (assuming that the time period between introduction of the device and compression is not overly long).

In other embodiments, the therapeutic-agent-containing region comprises a charged therapeutic agent within an ion-conductive polymeric region. Ion-conductive polymeric regions permit movement of ions, and in the present invention, permit movement of charged therapeutic agents. In addition to allowing ion movement, ion-conductive polymeric regions are also capable of maintaining therapeutic agents in an ionized form (via a process that is sometimes referred to as "solvation"), as opposed to a charge-neutral form (e.g., in non-ionized acid, base, salt, etc., form). Charge-neutral species are generally not transported in response to an electric field (although they may experience diffusion in response to a concentration gradient). Polymers suitable for maintaining therapeutic agents in ionized form commonly have cation and/or anion coordinating sites, which are capable of forming complexes with ions, or they are themselves ionized. Suitable ion-conductive homopolymers and copolymers may be selected, for example, from the following: (a) polyethers, such as polyethylene oxide (PEO) (also referred to as polyethylene glycol, particularly at lower molecular weights), polypropylene oxide (PPO), copolymers comprising ethylene oxide and copolymers comprising propylene oxide, including poly(ethylene oxide-co-propylene oxide), (b) polysiloxanes such as block copolymers of dimethyl siloxane and ethylene oxide, urethane crosslinked networks of poly(dimethyl siloxane-graft-ethylene oxide), and copolymers based on poly(methyl hydrosiloxane), poly(ethylene glycol) monomethyl ether and poly(ethylene glycol), see, e.g., Liang W-J. et al., "Morphology and Ionic Conductivity Studies of Hybrid Electrolytes based on Epoxide-Crosslinked Polysilane/Polyether Networks,"*Macromol. Chem. Phys.* 2004, 205, 600-610, (c) polyphosphazenes such as methoxy ethoxy ethoxy polyphosphazene (MEEP), (d) poly(vinyl pyrrolidines), (e) polyacrylates and polymethacrylates such as poly(methoxy ethoxy ethyl methacrylate) (polyMEEMA) and poly[(co-carboxy) oligooxyethylene methacrylate], (f) poly(crown ethers), (g) polyelectrolytes, for instance itaconates such as poly[diethoxy(3)methyl itaconate] and poly(di-poly(propylene glycol) itaconate), succinates such as poly(ethylene succinate), and adipates such as poly(ethylene adipate), (h) other polymers such as poly(vinyl alcohols), poly(ethylene imines), poly(alkylene sulphides), poly(propiolactones), cellulose acetates, poly(vinyl methyl ketones), poly(hexamethylene vinylenes), poly(styrenes), poly(2-ethyl-2-oxazoline) and blends thereof, among many others. Optimal homopolymers and copolymers for supporting ionization and transport of charged therapeutic agents within ion-conducting polymeric regions for use in the present invention will vary from therapeutic agent to therapeutic agent, with appropriate polymers for a given therapeutic agent being readily determined by those of ordinary skill in the art.

As noted above, the present invention provides medical devices that comprise a piezoelectric material. When a mechanical stress is applied to the piezoelectric material, a voltage is created between the first and second conductive regions, which voltage may be used to initiate or increase therapeutic agent release.

In various embodiments the mechanical stress that is applied is a compressive stress. Compressive stress may be provided in various ways. For example, compressive stress may be provided using a suitable mechanical arrangement. For instance, compression may be applied using a device such as a pressure actuated device (e.g., a device comprising a balloon), an electrically actuated device (e.g., a device comprising an electroactive polymer actuator), a temperature actuated device (e.g., a device comprising a shape memory metal such as Nitinol or a shape memory polymer or copolymer), and so forth. In certain embodiments (e.g., in the case of a drug delivery patch), pressure may be directed applied by the hands of a healthcare provider at the time of application. Compressive stress may also be effected by the body of the subject into which the device is implanted or inserted, for example, compressive stress may be (repeatedly) applied by the subject's beating heart (e.g., by the creation of systolic pressure). In some embodiments, compressive stress may be effected by the patient's body weight, for instance, a drug delivery device may be positioned between the bones (e.g., in the region of the knee, ankle, hip) or a drug delivery device may be positioned at normal pressure points on the body including the bottom of the feet, palms, buttocks and back, among others.

Examples of medical devices which can be provided in accordance with the invention vary widely and include medical devices for exterior application to the body such as patches for delivery of therapeutic agent to intact skin and broken skin (including wounds) and implantable or insertable medical devices, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts, etc.), vascular access ports, dialysis ports, catheters (e.g., urological catheters or vascular catheters such as balloon catheters and various central venous catheters), guide wires, Vascular Closure devices, balloons, filters (e.g., vena cava filters and mesh filters for distal protection devices), embolization devices including cerebral aneurysm filler coils (including Guglielmi detachable coils and metal coils), embolic agents, tissue bulking devices, septal defect closure devices, drug depots that are adapted for placement in an artery for treatment of the portion of the artery distal to the device, myocardial plugs, patches, leads including pacemaker leads, defibrillation leads and coils, neurostimulation leads such as spinal cord stimulation leads, deep brain stimulation leads, peripheral nerve stimulation leads, cochlear implant leads and retinal implant leads, pulse generators, ventricular assist devices including left ventricular assist hearts and pumps, total artificial hearts, shunts, valves including heart valves and vascular valves, anastomosis clips and rings, cochlear implants, tympanostomy tubes, thoracic drainage tubes, nephrostomy tubes, and tissue engineering scaffolds for cartilage, bone, skin, nerve (e.g., for neural pathway regeneration, including the spinal cord,), and other in vivo tissue regeneration, sutures, suture anchors, tissue staples and ligating clips at surgical sites, cannulae, metal wire ligatures, urethral slings, hernia "meshes", artificial ligaments, tacks for ligament attachment and meniscal repair, joint prostheses, spinal discs and nuclei, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants, contact lenses, interocular lenses, punctum plugs, glaucoma shunts, or other devices that are implanted or inserted into the body.

Preferred subjects are vertebrate subjects, for example, humans, livestock and pets.

"Therapeutic agents", "pharmaceuticals," "pharmaceutically active agents", "drugs" and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Exemplary therapeutic agents for use in conjunction with the present invention may be selected, for example, from the following, among others: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, and (gg) VLA-4 antagonists and VCAM-1 antagonists.

Numerous therapeutic agents, not necessarily exclusive of those listed above, have been identified as candidates for vascular treatment regimens, for example, as agents targeting restenosis (antirestenotics). Such agents are useful for the practice of the present invention and may be selected, for example, from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/ antioxidants such as probucol, vitamins C and E, ebselen, trans-retinoic acid, SOD (orgotein) and SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine antagonists/ analogs (e.g., 6-mercaptopurine and pro-drugs of 6-mercaptopurine such as azathioprine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, and epothilone), caspase activators, proteasome inhibitors, angiogenesis inhibitors (e.g., endostatin, angiostatin and squalamine), sirolimus, everolimus, tacrolimus, zotarolimus, biolimus, cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Preferred therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, biolimus, tacrolimus and zotarolimus, Epo D, dexamethasone, purine antagonists/analogs such as 6-mercaptopurine, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/ protein, imiquimod, human apolioproteins (e.g., AI-AV), growth factors (e.g., VEGF-2), as well derivatives and pro-drugs of the forgoing, among others.

Numerous additional therapeutic agents useful for the practice of the present invention are also disclosed in U.S. Pat. No. 5,733,925 to Kunz, the entire disclosure of which is incorporated by reference.

In some embodiments, the therapeutic agent may be a charged therapeutic agent. By "charged therapeutic agent" is meant a therapeutic agent that has an associated charge, in which case it may be introduced into the coating during the coating formation process.

A therapeutic agent may have an associated charge, for example, because it is inherently charged (e.g., because it has acidic and/or or basic groups, which may be in salt form). A few examples of inherently charged cationic therapeutic agents include amiloride, digoxin, morphine, procainamide, and quinine, among many others. Examples of anionic therapeutic agents include heparin and DNA, among many others.

A therapeutic agent may have an associated charge because it has been chemically modified to provide it with one or more charged functional groups. For instance, conjugation of water insoluble or poorly soluble drugs, including anti-tumor agents such as paclitaxel, to hydrophilic polymers has been carried out in order to solubilize the drug (and in some cases to improve tumor targeting and reduce drug toxicity). Similarly cationic or anionic versions of water insoluble or poorly soluble drugs have also been developed. Taking paclitaxel as a specific example, various cationic forms of this drug are known, including paclitaxel N-methyl pyridinium mesylate and paclitaxel conjugated with N-2-hydroxypropyl methyl amide, as are various anionic forms of paclitaxel, including paclitaxel-poly(l-glutamic acid), paclitaxel-poly(l-glutamic acid)-PEO. See, e.g., U.S. Pat. No. 6,730,699; Duncan et al., *Journal of Controlled Release* 74 (2001) 135; Duncan, *Nature Reviews/Drug Discovery, Vol.* 2, May 2003, 347; Jaber G. Qasem et al, *AAPS PharmSciTech* 2003, 4(2) Article 21. In addition to these, U.S. Pat. No. 6,730,699, also describes paclitaxel conjugated to various other charged polymers (e.g., polyelectrolytes) including poly(d-glutamic acid), poly(dl-glutamic acid), poly(l-aspartic acid), poly(d-aspartic acid), poly(dl-aspartic acid), poly(l-lysine), poly(d-lysine), poly (dl-lysine), copolymers of the above listed polyamino acids with polyethylene glycol (e.g., paclitaxel-poly(l-glutamic acid)-PEO), as well as poly(2-hydroxyethyl 1-glutamine), chitosan, carboxymethyl dextran, hyaluronic acid, human serum albumin and alginic acid. Still other forms of paclitaxel include carboxylated forms such as 1'-malyl paclitaxel sodium salt (see, e.g. E. W. DAmen et al., "Paclitaxel esters of malic acid as prodrugs with improved water solubility," *Bioorg Med. Chem.*, 2000 February, 8(2), pp. 427-32). Polyglutamate paclitaxel, in which paclitaxel is linked through the hydroxyl at the 2' position to the Δ carboxylic acid of the poly-L-glutamic acid (PGA), is produced by Cell Therapeutics, Inc., Seattle, Wash., USA. (The 7 position hydroxyl is also available for esterification.) This molecule is said to be cleaved in vivo by cathepsin B to liberate diglutamyl paclitaxel. In this molecule, the paclitaxel is bound to some of the carboxyl groups along the backbone of the polymer, leading to multiple paclitaxel units per molecule. For further information, see, e.g., R. Duncan et al., "Polymer-drug conjugates, PDEPT and PELT: basic principles for design and transfer from the laboratory to clinic," *Journal of Controlled Release* 74 (2001) 135-146, C. Li, "Poly(L-glutamic acid)-anticancer drug conjugates," *Advanced Drug Delivery Reviews* 54 (2002) 695-713; Duncan, *Nature Reviews/Drug Discovery*, Vol. 2, May 2003, 347; Qasem et al, *AAPS PharmSciTech* 2003, 4(2) Article 21; and U.S. Pat. No. 5,614,549. Such strategies may be applied to a host of other therapeutic agents, including anti-restenotic agents other than paclitaxel, for instance, everolimus or biolimus, among others.

Using the above and other strategies, paclitaxel and many other therapeutic agents may be covalently linked or otherwise associated with a variety of charged species, including charged polymers, thereby forming charged drugs and prodrugs.

A therapeutic agent may also have an associated charge because it is attached to a charged particle or because it is encapsulated within a charged particle, for example, encapsulated within a charged nanocapsule or within a charged micelle, among others. A therapeutic agent may be provided within a charged capsule, for example, using layer-by-layer techniques in which capsules are formed from alternating layers of polyanions and polycations such as those described above and in Pub. No. US 2005/0129727 to Weber et al. For a specific example of such a technique, see I. L. Radtchenko et al., "A novel method for encapsulation of poorly water-soluble drugs: precipitation in polyelectrolyte multilayer shells," *International Journal of Pharmaceutics*, 242 (2002) 219-223.

Using the above and other techniques, a wide range of therapeutic agents may be provided with associated charges.

Several specific embodiments of the invention will now be described with reference to the drawings.

Figure 1B:
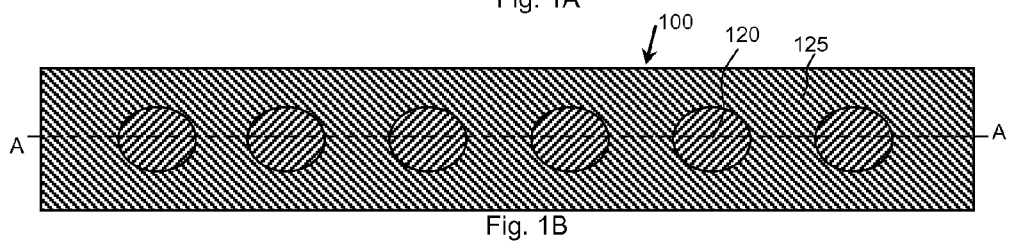
FIG. 1B is a partial schematic top view of a medical device in accordance with an embodiment of the invention at a point during its manufacture.

FIG. 1B is a schematic top view of a medical device 100 in accordance with an embodiment of the invention. FIG. 1A is a cross sectional view of FIG. 1B, taken along line A-A. Such a structure 100 may correspond, for instance, to a portion of an expandable medical device such as a balloon or stent. (Conversely, a suitable force may be generated using a contractable medical device, among other possibilities.) The structure 100 includes, for example, a substrate 110, a first conductive layer 120, a piezoelectric layer 130 and an upper conductive layer 125.

Figure 1C:
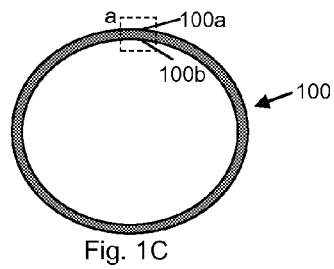
FIG. 1C is a schematic cross-section of a balloon, in accordance with an embodiment of the invention. The partial cross-sectional area a in FIG. 1C may correspond, for example, to a partial schematic cross-sectional view like that of FIG. 1A in certain embodiments.

FIG. 1C is a schematic cross-section of a balloon 100, in accordance with an embodiment of the invention. In certain embodiments, the partial cross-sectional area a of the balloon 100 in FIG. 1C may correspond, for example, to a partial schematic cross-section like that of FIG. 1A wherein the top surface 100a of FIG. 1A corresponds to the outer surface 100a of the balloon 100 of FIG. 1C and the bottom surface 100b of FIG. 1A corresponds to the inner surface 100b of the balloon 100 of FIG. 1C.

A method for the manufacture of the structure of FIGS. 1A-1B will now be briefly described. On a substrate 110 (e.g., a PEBAX balloon, polymeric stent, etc.) is deposited a first conductive layer 120 (e.g., a layer of a metal or metal alloy such as gold, platinum, etc.). For example, such a layer 120 may be deposited via physical vapor deposition (PVD). Then a piezoelectric layer 130, for example, a layer of poly(vinylidene fluoride-co-trifluoroethylene), also referred to herein as P(VDF-TrFE), is deposited on the conductive layer 120. For instance, a melt or a solution containing the P(VDF-TrFE) may be coated onto the first conductive layer 120. An upper conductive layer 125 (e.g., a layer of a metal or metal alloy such as gold, platinum, etc.) is deposited on the piezoelectric layer 130, for example, using PVD. A desired pattern may be formed by selectively removing material from the upper conductive layer 125 and the piezoelectric layer 130, for instance, using masking and plasma etching techniques analogous to those used in the semiconductor art. As indicated above, FIG. 1B is a top view of the structure of FIG. 1A and illustrates the fact that a series of cylindrical cavities are formed in the piezoelectric material layer 130 and upper conductive layer 125.

The piezoelectric material layer 130 in the structure of FIGS. 1A and 1B can then be poled using a suitable technique. As discussed further below in conjunction with FIGS. 4A-4B, the poling direction is such that a positive charge (and thus an anodic/oxidizing potential) can be generated at the upper conductive layer 125 when the piezoelectric material layer 130 is compressed (in the direction shown by the arrows in FIG. 4A).

Figure 2A:
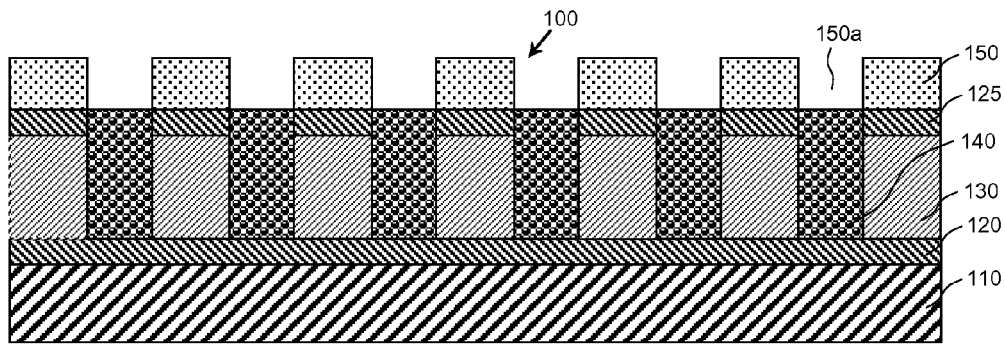
FIG. 2A is a partial schematic cross-sectional view of the device of FIG. 2B, taken along line A-A.
Figure 2B:
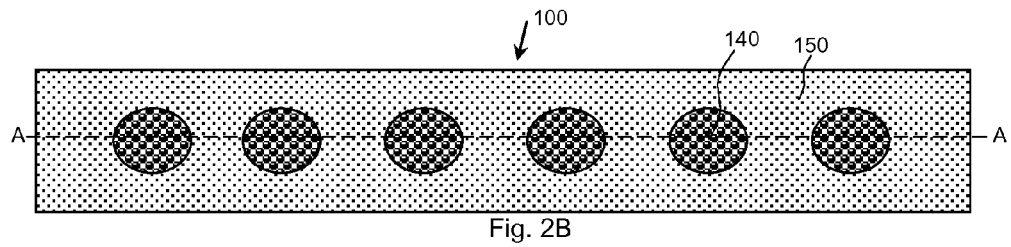
FIG. 2B is a partial schematic top view of a medical device like that of FIG. 1B upon further processing, in accordance with an embodiment of the invention.

Turning now to FIGS. 2A-2B, a conductive polymer layer 150 is then applied to the upper conductive layer 125. For example, a layer of polypyrrole (PPy) doped with a large negative immobile ion such as dodecylbenzenesulfonate (DBS) may be formed by electropolymerization of PPy in oxidized form (PPy$^+$) on the upper conductive layer 125 from a solution containing pyrrole and DBS$^-$. The above-noted cylindrical cavities can then be filled with a therapeutic agent 140 to form the structure shown in cross-section in FIG. 2A and in top view in FIG. 2B. For example, the therapeutic agent 140 may be in substantially pure form or may be admixed with an excipient material.

Figure 3A:
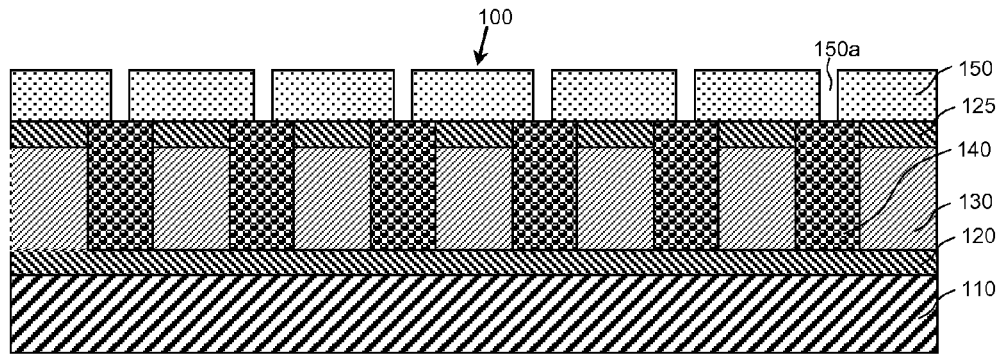
FIG. 3A is a partial schematic cross-sectional view of the device of FIG. 3B, taken along line A-A.
Figure 3B:
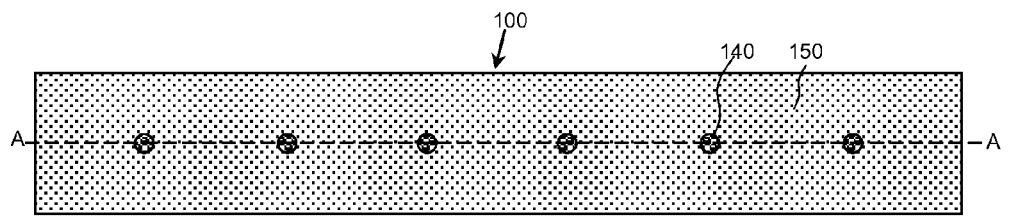
FIG. 3B is a partial schematic top view of the medical device of FIG. 2B after apertures in the device have been substantially closed.

Turning to FIGS. 3A-3B, the conductive polymer layer 150 may then be swelled using a suitable technique, thereby closing or reducing the diameter of the apertures 150a in the conductive polymer layer 150. (The structure of FIGS. 2A-2B is shown, post-swelling, in cross-section in FIG. 3A and in top view in FIG. 3B.) For instance, a DBS-doped PPy layer 150 can be swelled by placing it in contact with a solution containing small mobile cations (e.g., saline, a potassium chloride solution, etc.) and applying a potential between the upper conductive layer 125 and a counter-electrode positioned in the solution (not shown). By applying a suitable potential, the polypyrrole in the DBS-doped PPy layer 150 is converted to reduced form)(PPy$^0$), causing positively charged mobile cations in the solution flow into the DBS-doped PPy layer 150 (to offset the net negative charge associated with the immobilized DBS$^-$ anions), thereby swelling the DBS-doped PPy layer 150.

Figure 4A:
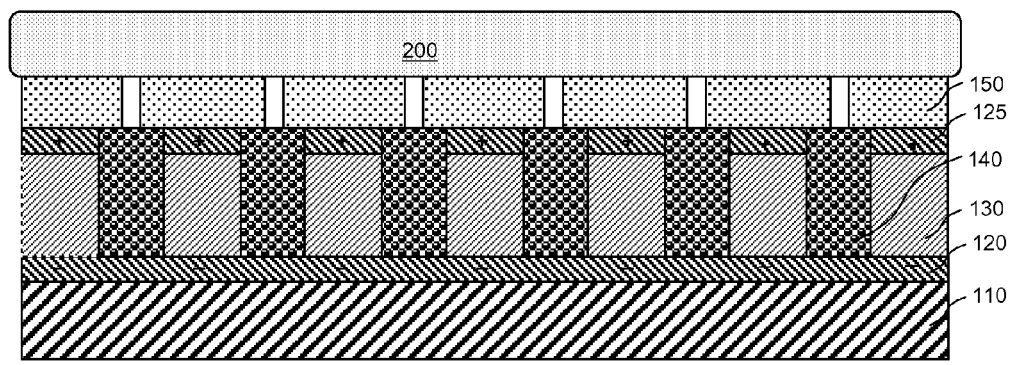
FIGS. 4A and 4B are schematic partial cross-sectional views showing the device of FIG. 3B within the body, before and after compression of the device, respectively.
Figure 4B:
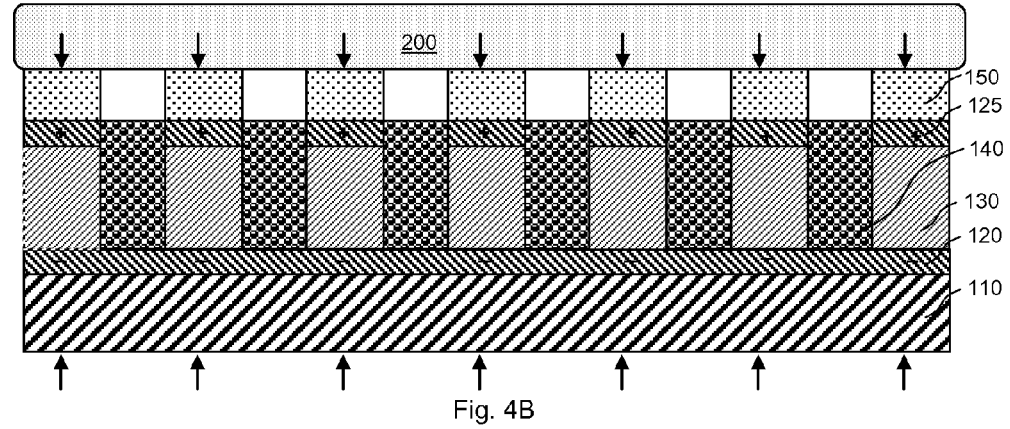

The structure of FIG. 3A is then inserted into the body and placed adjacent to body tissue 200, as show schematically in FIG. 4A. The structure of FIG. 4A, specifically the piezoelectric layer 130 between the conductive layers 120, 125, is then compressed in vivo, for example, by pressing the structure against tissue 200 as shown in FIG. 4B (the compression is represented by the arrows in FIG. 4B). For example, as indicated above, the structure shown may be a portion an expandable balloon that presses the structure against tissue 200 in vivo. Upon compression of the previously-poled piezoelectric layer 130, the upper conductive layer 125 on the upper surface becomes positively changed, leading to oxidation of the polypyrrole (PPy$^+$), and resulting in the expulsion of the small mobile cations. As a result, the conductive polymer layer 150 shrinks, causing the apertures in the layer to widen as shown in FIG. 4B. This is gate-opening effect, enhancing the ability of the therapeutic agent 140 to diffuse from the structure and into contact with the tissue.

Figure 5A:
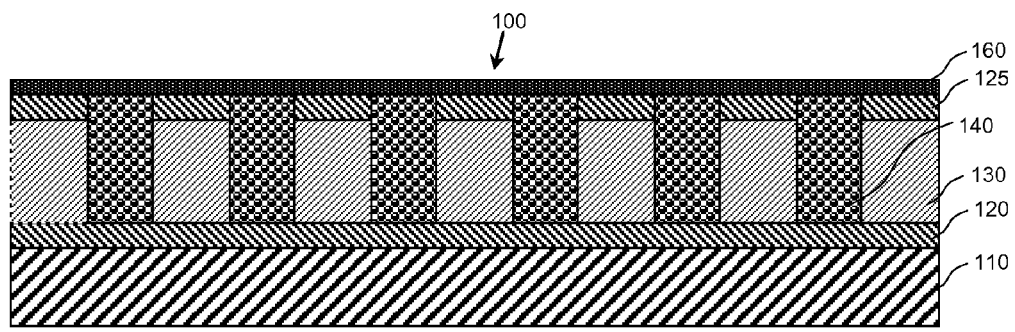
FIG. 5A is a partial schematic cross-sectional view of a medical device like that of FIG. 1B after further processing, in accordance with an embodiment of the invention.
Figure 5B:
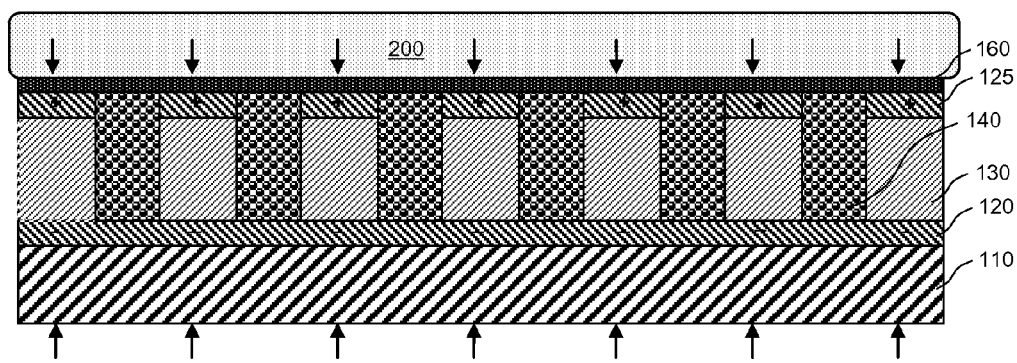
FIG. 5B shows the device of FIG. 5A upon compression of the device within the body.

In another embodiment of the invention shown in FIG. 5A, a structure like that shown in FIGS. 1A-1B is first formed. Subsequently, the cylindrical cavities are filled with a suitable therapeutic agent 140, followed by the application of a layer of relatively corrosion-prone material 160 such as calcium, magnesium (e.g., for a balloon) or iron (e.g., for a stent). Such a layer may be formed, for example, using PVD. The resulting structure is shown in FIG. 5A. When the structure of FIG. 5A is compressed in vivo, for example by pressing the structure against tissue 200 as shown in FIG. 5B, the upper surface of the previously-poled piezoelectric layer 130 becomes positively changed, leading to oxidation of the corrosion-prone material 160, thereby accelerating corrosion of the same. The therapeutic agent is released once oxidation/corrosion begins to form pores/holes in the layer 160 though which the therapeutic agent can diffuse.

Figure 5C:
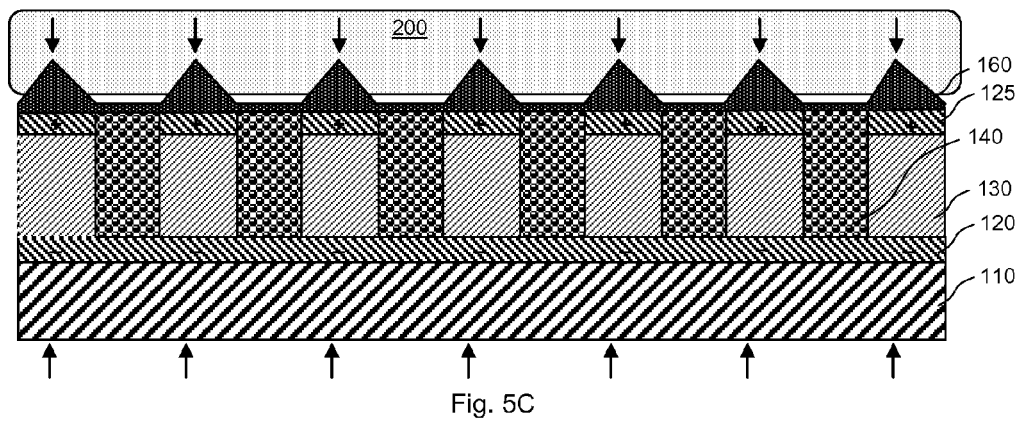
FIG. 5C is a partial schematic cross-sectional view of a medical device like that of FIG. 5B (except that the device is provided with sharp tissue-penetrating members) upon compression of the device within the body.

In a related embodiment, tissue penetrating members (e.g., cutting blades or piercing needles) are created from the corrosion-prone material 160 in the regions over the piezoelectric layer 130, as shown in FIG. 5C. (Alternatively, tissue penetrating members may be formed from a different material, for example, stainless steel or another less corrosion-prone material.) The areas of the corrosion-prone material 160 over the therapeutic agent 140 are made thin, thereby allowing these areas to be readily breached by oxidation/corrosion.

Figure 5D:
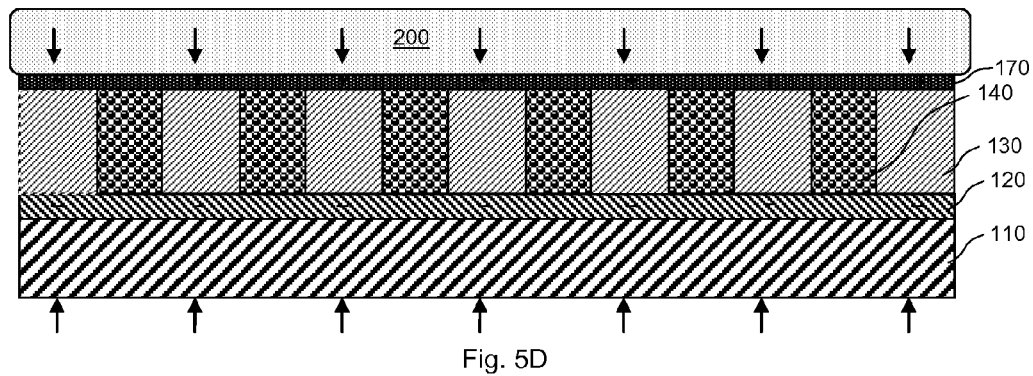
FIG. 5D is a partial schematic cross-sectional view of a medical device in accordance with another embodiment of the invention, upon compression of the device within the body.

As seen in FIG. 5D, in certain embodiments, the upper conductive layer 125 and corrosion-prone material 160 structures of FIG. 5B (of FIG. 5C) may be replaced with a single region of corrosion-prone metal 170, which acts both as a current collector for the piezoelectric layer 130 and as a corrodible barrier to temporarily retain the drug 140.

In the preceding embodiments, the charge generated upon compression of the piezoelectric material is used to create and/or enlarge an aperture (e.g., by shrinking an aperture-containing material, by corroding a material, etc.). In these embodiments, the therapeutic agent may be charged or uncharged.

Figure 6A:
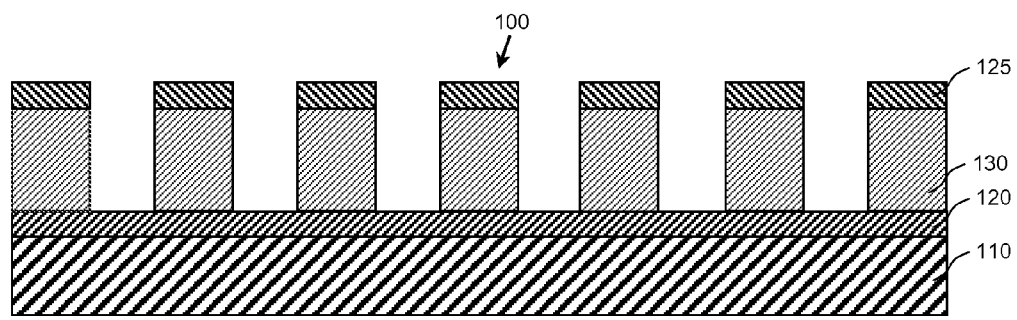
FIG. 6A is a partial schematic cross-sectional view of the device of FIG. 6B, taken along line A-A.
Figure 6B:
FIG. 6B is a partial schematic top view of a medical device in accordance with an embodiment of the invention, at an early point in its manufacture.

In other embodiments, the charge generated in the piezoelectric material upon compression may be used to drive away or retain the therapeutic agent. For example, a structure similar to that shown in FIG. 1A may be formed as shown in FIG. 6A. However, since partially/totally sealed chambers are not required in these embodiments, the top view of the structure may be as shown in FIG. 6B. Rather than forming a piezoelectric layer 130 that contained a series of cylindrical cavities (as in FIGS. 1A-1B), in FIGS. 6A-6B, a series of piezoelectric pillars 130 are formed and capped with a discontinuous conductive layer 125 in FIGS. 6A-6B. A therapeutic-agent-containing layer 140 is then formed over the conductive layer 120 as shown in FIGS. 7A-7B.

Figure 7A:
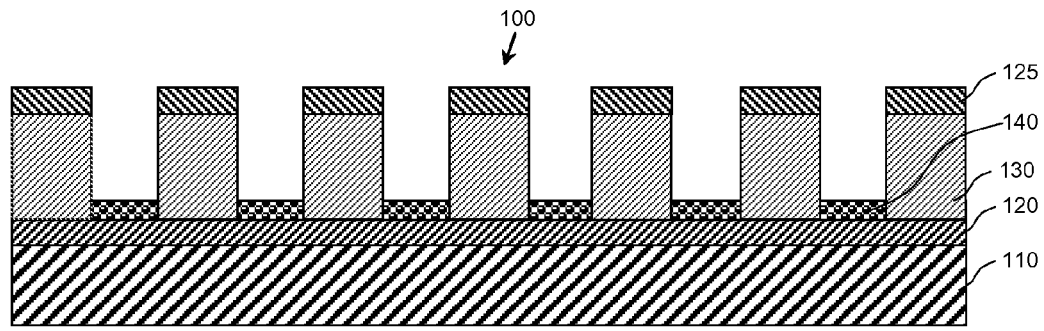
FIG. 7A is a partial schematic cross sectional view of the device of FIG. 7B, taken along line A-A.
Figure 7B:
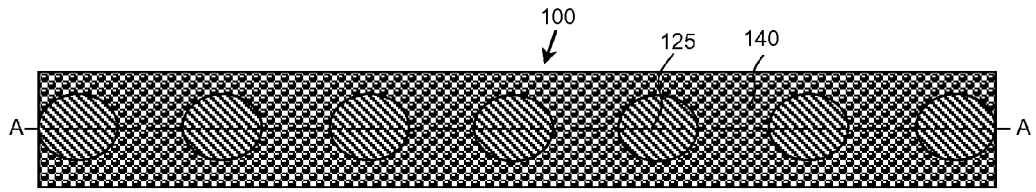
FIG. 7B is a partial schematic top view of a medical device like that of FIG. 6B upon further processing, in accordance with an embodiment of the invention.
Figure 8:
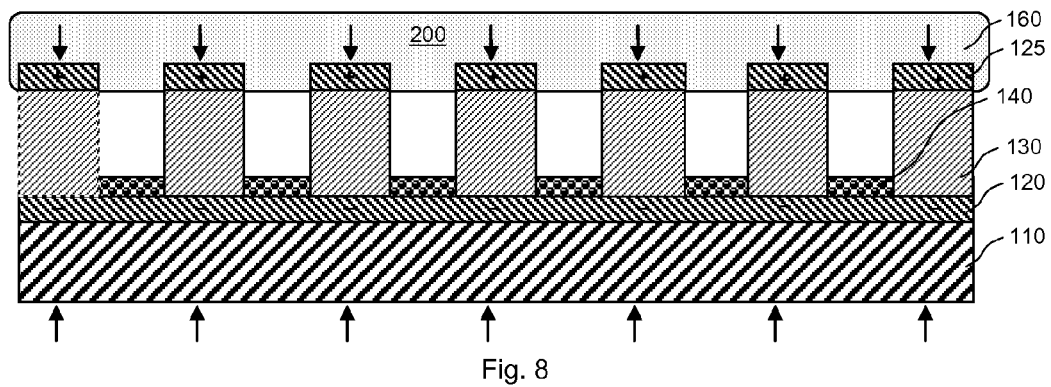
FIG. 8 is a schematic partial cross-sectional view showing the device of FIG. 7A upon compression of the device within the body.

When the structure of FIGS. 7A-7B is subsequently compressed in vivo, for example by expanding substrate 110 into tissue 200 as shown in FIG. 8, the lower metallic layer 120 becomes negatively charged relative to the upper metal regions 125. If a negatively charged therapeutic agent is provided in the therapeutic-agent-containing layer 140, the electric field will drive the therapeutic agent in the direction of the tissue 200. If a positively charged therapeutic agent is provided, the electric field will tend to hold the therapeutic agent in the vicinity of the lower metallic layer 120 (i.e., in the therapeutic-agent-containing layer 140).

Figure 9:
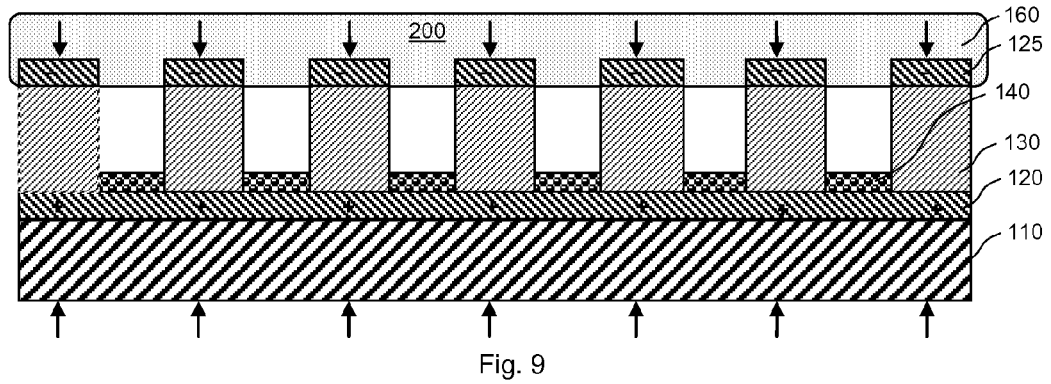
FIG. 9 shows a medical device upon disposition of the device within the body. The device of FIG. 9 is like that of FIG. 8 except that the poling axis of the piezoelectric layer is reversed.

FIG. 9 is similar to FIG. 8, except that the poling axis in FIG. 9 is reversed relative to that of FIG. 8. Consequently, when the structure of FIG. 9 is compressed in vivo (e.g., by expanding substrate 110 in the direction of tissue 200), the lower metallic layer 120 becomes positively charged relative to the upper metal regions 125. If a positively charged therapeutic agent is provided in the therapeutic-agent-containing layer 140, the electric field will drive the therapeutic agent in the direction of the tissue 200. If a negatively charged therapeutic agent is provided in the therapeutic-agent-containing layer 140, the electric field will tend to hold the therapeutic agent in the vicinity of the lower metallic layer 120 (i.e., in the therapeutic-agent-containing layer 140).

Figure 10A:
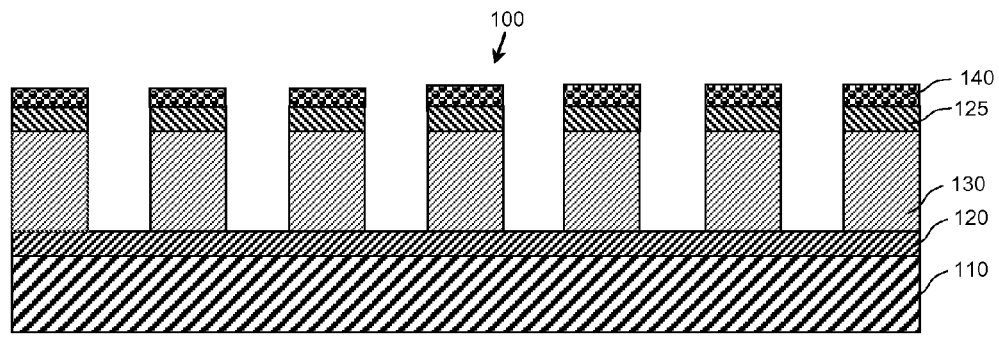
FIG. 10A is a partial schematic cross-sectional view of the device of FIG. 10B, taken along line A-A.
Figure 10B:
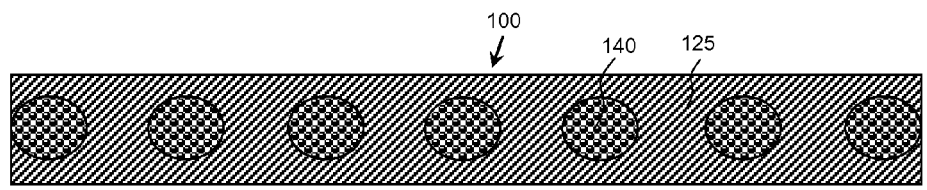
FIG. 10B is a partial schematic top view of a medical device like that of FIG. 6B upon further processing, in accordance with an embodiment of the invention.

In another embodiment, as is shown in FIGS. 10A-10B, a discontinuous therapeutic-agent-containing layer 140 may be formed over the upper discontinuous conductive layer 125 of the device of FIGS. 6A-6B.

Figure 11:
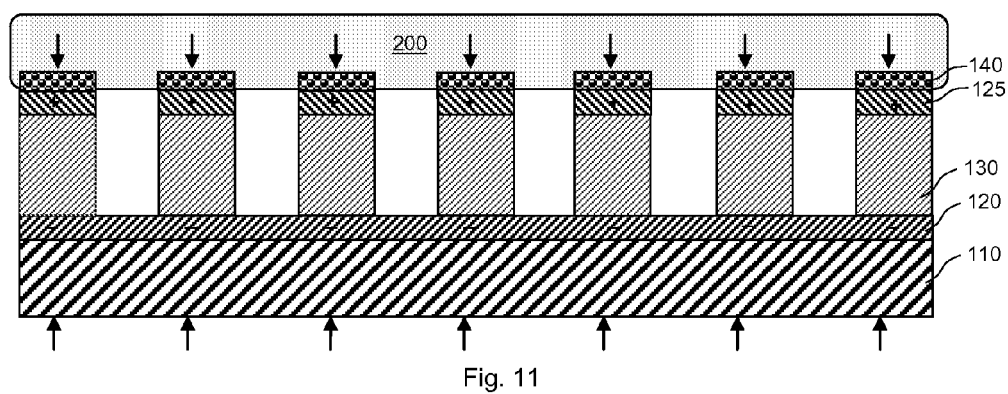
FIG. 11 is a schematic partial cross-sectional view showing the device of FIG. 10A upon compression of the device within the body.

When the structure of FIGS. 10A-10B is compressed in vivo as shown in FIG. 11 (e.g., by expanding substrate 110 into tissue 200), the upper conductive layer 125 becomes positively charged relative to the lower conductive layer 120. If a positively charged therapeutic agent is provided, the electric field will tend to drive the therapeutic agent from the therapeutic-agent-containing layer 140. If a negatively charged therapeutic agent is provided, the electric field will tend to hold the therapeutic agent in the vicinity of the therapeutic-agent-containing layer 140. As above, the poling direction may be reversed in other embodiments, with an opposite effect on positively and negatively charged therapeutic agents.

As noted above, in certain embodiments of the invention, a conductive substrate 110 is employed. The use of a conductive substrate 110 allows for the removal of the lower conductive layer 120 shown in FIG. 11. See, e.g., FIG. 14. For example, the conductive substrate 110 may correspond to a metallic stent, among many other possibilities.

Figure 15:
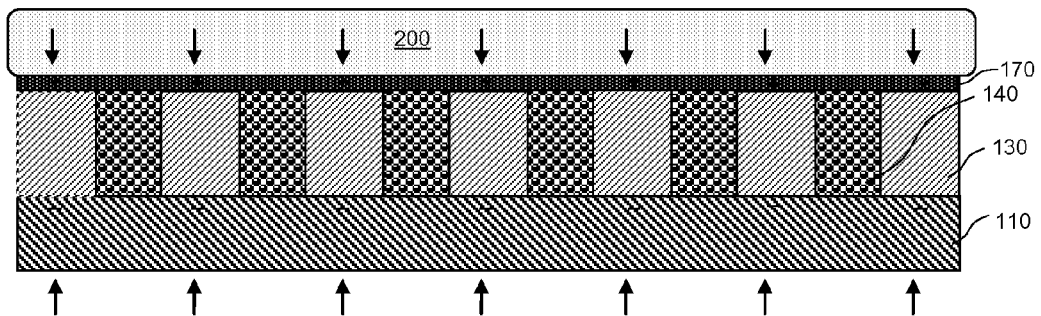

Similarly, in contrast to FIG. 5D, a structure may be formed that comprises a conductive substrate 110, a piezoelectric layer 130, series of cylindrical cavities filled with a therapeutic agent 140, and a corrosion-prone metal layer 170, as shown in FIG. 15.

Figure 14:
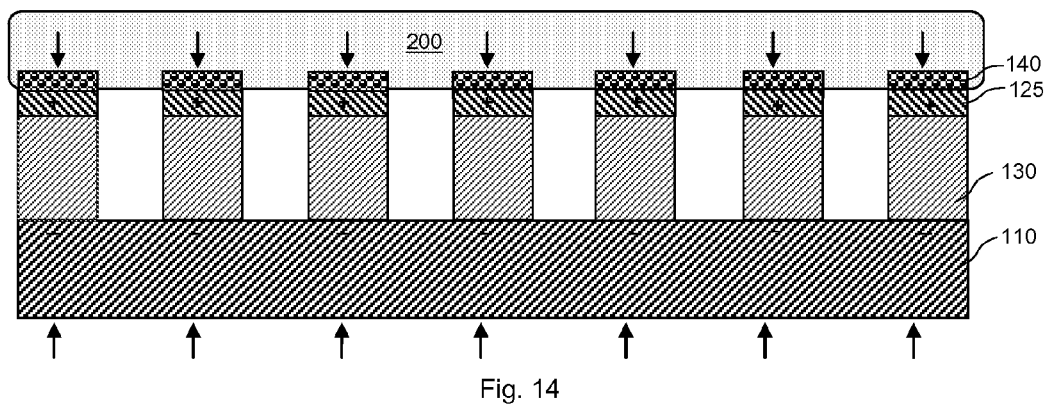
FIGS. 14 and 15 are schematic partial cross-sectional views showing two medical devices in accordance with an embodiment of the invention, upon compression of the devices within the body.

In this regard, in some embodiments, the present invention is directed to medical devices that are completely biodegradable. For example, a medical device as shown in FIG. 14 or FIG. 15 may comprise, for instance, a biodegradable substrate (e.g., iron, iron alloy, magnesium, magnesium alloy, etc.), a biodegradable piezoelectric ceramic layer 130 (e.g., a magnesium zinc oxide ceramic, ferrite base piezoelectric, etc,), a biodegradable upper conductive layer 125 or corrosion-prone layer 170 (e.g., iron, iron alloy, magnesium, magnesium alloy, etc.), and a biodegradable therapeutic agent 140 (e.g., pure drug, drug dispersed in a porous or non-porous layer of biodegradable material, etc.).

Figure 12:
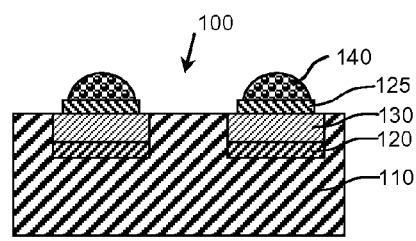
FIGS. 12 and 13 are partial schematic cross-sectional views of medical devices in accordance with two embodiments of the invention.
Figure 13:
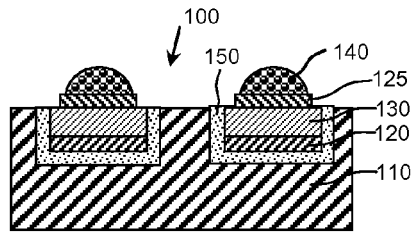

FIG. 12 is a partial schematic cross-sectional view of a medical device 100 in accordance with another embodiment of the invention. The device is somewhat analogous to the device of FIG. 10A, except that the lower conductive layer 120 and piezoelectric regions 130 are recessed in the substrate 110. (The upper conductive layer 125 and therapeutic agent 140 are not recessed in the substrate 110.) The substrate 110 in FIG. 12 is not electrically conductive. Accordingly, charge separation can be maintained between the top and bottom surfaces of the piezoelectric regions 130 upon compression of the same. In other embodiments where the substrate 110 is electrically conductive, an insulating region 150 may be employed in the medical device 100 to maintain charge separation upon compression as shown in FIG. 13.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising a therapeutic-agent-containing region, a shrinkable and swellable barrier layer having an aperture disposed over the therapeutic-agent-containing region wherein the aperture increases in size when the barrier layer shrinks and decreases in size when the barrier layer swells, a piezoelectric region, a first conductive region disposed on a first surface of the piezoelectric region and a second conductive region disposed on a second surface of the piezoelectric region, wherein said first and second conductive regions are not in contact with one another, wherein when said device is administered to a subject and said piezoelectric region is subjected to mechanical stress, a voltage is created between the first and second conductive regions, wherein the barrier layer shrinks and the aperture is increased in size when the voltage is created, thereby initiating or increasing a rate of release of therapeutic agent from said therapeutic-agent-containing region into the subject.

2. The medical device of claim 1, wherein said voltage is created when the piezoelectric region is subjected to mechanical compression.

3. The medical device of claim 2, wherein the first conductive region corresponds to a conductive substrate or the first conductive region corresponds to a layer of conductive material that is formed on a non-conductive substrate.

4. The medical device of claim 2, wherein the piezoelectric region is in the form of a piezoelectric layer that is disposed on an upper surface of the first conductive region and wherein the second conductive region is in the form of a conductive layer that is disposed on an upper surface of the piezoelectric layer.

5. The medical device of claim 2, wherein the medical device is expandable or contractable in vivo.

6. The medical device of claim 5, wherein the medical device is a medical balloon and wherein the therapeutic agent is an anti-restenotic agent.

7. The medical device of claim 5, wherein the medical device is a vascular stent and wherein the therapeutic agent is an anti-restenotic agent.

8. The medical device of claim 1, wherein said barrier layer comprises a conductive polymer.

9. The medical device of claim 1, wherein the therapeutic agent is disposed within a plurality of cavities beneath the barrier layer and wherein the barrier layer comprises at least one aperture positioned over each of said cavities.

10. The medical device of claim 1, wherein the medical device is biodegradable.

11. The medical device of claim 1, wherein the piezoelectric region comprises a piezoelectric polymeric material.

12. The medical device of claim 1, wherein the piezoelectric region comprises a piezoelectric ceramic material.

13. The medical device of claim 1, wherein the piezoelectric region comprises a piezoelectric ceramic-polymer composite material.

14. The medical device of claim 1, wherein the medical device is a stent that comprises a shape memory alloy.

15. A medical device which is a balloon or a stent, said medical device comprising (a) a therapeutic agent, (b) a piezoelectric region, (c) a first conductive region disposed on a first surface of the piezoelectric region, wherein the first conductive region corresponds to a conductive substrate or the first conductive region corresponds to a layer of conductive material that is formed over a non-conductive substrate, and (d) a second conductive region disposed on a second surface of the piezoelectric region, wherein said first and second conductive regions are not in contact with one another, wherein the piezoelectric region is in the form of a piezoelectric layer that is disposed on an upper surface of the first conductive region, wherein the second conductive region is in the form of a conductive layer that is disposed on an upper surface of the piezoelectric layer, wherein the therapeutic agent is disposed in one or more cavities that extend from an upper surface of the second conductive region and into said piezoelectric layer, wherein said medical device comprises a barrier layer comprising a conductive polymer that is disposed over the second conductive region and the one or more cavities, wherein the barrier layer comprises at least one aperture positioned over each of said one or more cavities, wherein when said device is administered to a subject and said piezoelectric region is subjected to mechanical compression, a voltage is created between the first and second conductive regions, and wherein the barrier layer shrinks and the at least one aperture is increased in size when the voltage is created between the first and second conductive regions thereby initiating or increasing a rate of release of the therapeutic agent from the device into the subject.

* * * * *